United States Patent
Milbocker et al.

(10) Patent No.: US 8,114,157 B2
(45) Date of Patent: Feb. 14, 2012

(54) REVERSIBLY GELLING POLYURETHANE COMPOSITION FOR SURGICAL REPAIR AND AUGMENTATION

(75) Inventors: Michael T. Milbocker, Holliston, MA (US); Jeffrey A. Wilson, Wrentham, MA (US)

(73) Assignee: Promethean Surgical Devices, LLC, East Hartford, CT (US)

( * ) Notice: Subject to any disclaimer, the term of this patent is extended or adjusted under 35 U.S.C. 154(b) by 873 days.

(21) Appl. No.: 12/162,039

(22) PCT Filed: Jan. 24, 2007

(86) PCT No.: PCT/US2007/001830
§ 371 (c)(1),
(2), (4) Date: Jul. 24, 2008

(87) PCT Pub. No.: WO2007/089484
PCT Pub. Date: Aug. 9, 2007

(65) Prior Publication Data
US 2009/0012462 A1 Jan. 8, 2009

Related U.S. Application Data

(60) Provisional application No. 60/762,302, filed on Jan. 26, 2006.

(51) Int. Cl.
*A61F 2/00* (2006.01)
(52) U.S. Cl. ............... 623/17.11; 606/113; 623/23.72
(58) Field of Classification Search ............ 606/110, 606/113; 623/11.11, 15.12, 17.11, 17.12, 623/17.16, 23.72; 604/57; 528/73; 424/78.37
See application file for complete search history.

(56) References Cited

U.S. PATENT DOCUMENTS

| | | | |
|---|---|---|---|
| 4,403,083 | A | 9/1983 | Marans et al. |
| 5,752,974 | A | 5/1998 | Rhee et al. |
| 2002/0010514 | A1 | 1/2002 | Burg et al. |
| 2002/0049503 | A1 | 4/2002 | Milbocker |
| 2003/0134294 | A1 | 7/2003 | Sandford et al. |
| 2003/0194505 | A1 | 10/2003 | Milbocker |
| 2004/0068078 | A1 | 4/2004 | Milbocker |
| 2005/0070913 | A1 | 3/2005 | Milbocker et al. |

OTHER PUBLICATIONS

Turri et al., Rheological properties and thermal transitions in millable polyurethane fluorelastomers, Polymer International, Apr. 2005, vol. 54, pp. 698-704.
Feitoza et al., Hydroxyproply methylcellulose: A better submucosal fluid cushion for endoscopic mucosal resection, Gastrointestinal Endoscopy, Jan. 2003, vol. 57, No. 1, pp. 41-47.
Stecevic et al., Gastric duplication cyst treated by endoscopic electrosurgical snare resection, Gastrointestinal Endoscopy, Apr. 2003, vol. 57, No. 4, pp. 615-616.

*Primary Examiner* — Eduardo C Robert
*Assistant Examiner* — David Comstock
(74) *Attorney, Agent, or Firm* — Rissman Hendricks & Oliverio LLP

(57) ABSTRACT

A new reversibly gelling polyurethane (RGP) polymer composition is described, as well as novel processes for its preparation, and its medical uses for filling spaces in tissue, or bulking tissue, or for restoring organ function. The novel RGP polymer forms a gel on standing, liquefies during shear and reversibly reforms a macroscopic gel on standing after being sheared. Methods of use include delivering the improved gel to a site on the body to fill voids or to augment local tissue bulk.

27 Claims, 1 Drawing Sheet

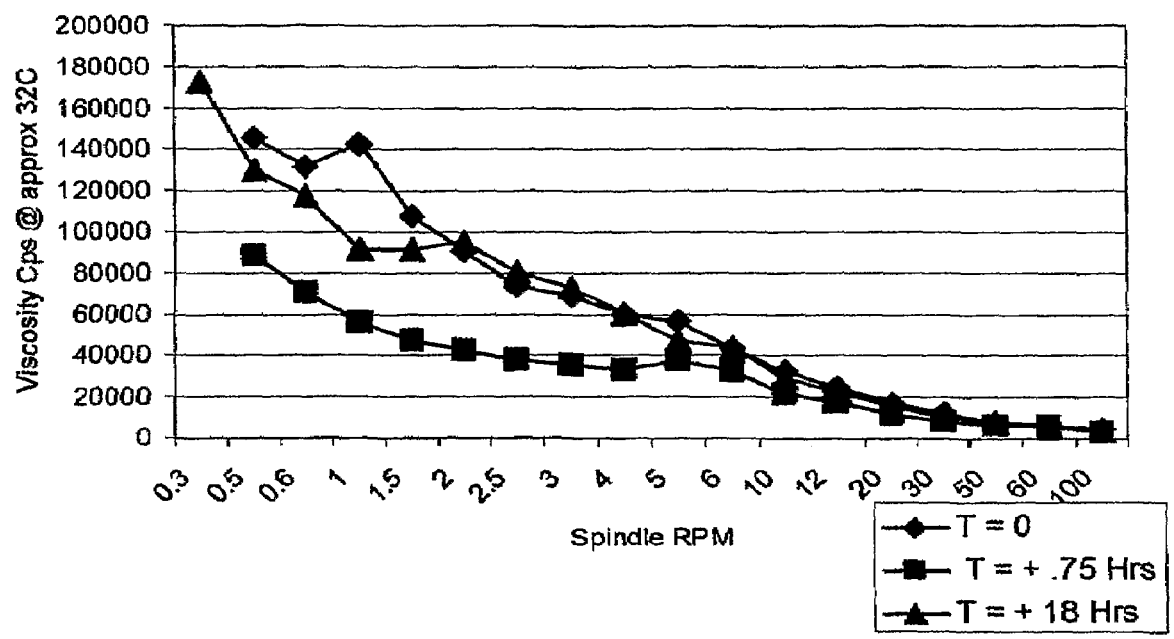

REVERSIBLY GELLING POLYURETHANE COMPOSITION FOR SURGICAL REPAIR AND AUGMENTATION

This application claims the benefit of the priority of co-pending U.S. provisional application 60/762,302, filed Jan. 26, 2006, which is incorporated herein by reference.

BACKGROUND OF THE INVENTION

We have previously described certain polyurethane materials and methods for forming an implant in situ, as described, for example, in US patents and publications U.S. Pat. Nos. 6,254,327, 6,296,607, 6,702,731, 7,044,982, 7,047,980, 2002-0049503, 2002-0049363, 2003-0135238, 2003-0194505, 2003-0188755, 2004-0068078, 2003-0135238, 2005-0129733, 2005-0070913, 2005-0187429, 2005-0215748, 2005-0247322 and 2006-01198816, each of which is incorporated herein by reference. The materials used are a small subset of the large number of polyurethane materials. Examples of polyurethane materials that are similar but are not believed to be suitable for implantation in the body include those described by U.S. Pat. Nos. 3,380,967; 3,607,822; 5,338,767; 6,255,433; and 2004/0076758. U.S. Pat. No. 3,923,926 to Kuroda et al describes a material formally similar to our preferred ranges, but which produce dissimilar results. U.S. Pat. Nos. 5,173,301, 4,994,542, 4,806,614, 4,740,534, and 5,173,301, to Matsuda and colleagues, describe polymerization of urethanes in situ in the body.

There are numerous medical conditions in which filling a space, or adding bulk to a tissue, is needed to alleviate the condition Tissue bulking is believed to be helpful in tightening sphincters, for example in the esophagus and bladder. U.S. Pat. No. 5,785,642 (Wallace et al.) describes a 3-part injectable polymer for treating incontinence. The patent claims improved resistance to migration, principally when compared with particulate injectables. The invention in 5,785,642 involves forming a polymer precipitate in situ from a solvent/polymer system. Since the solvent does not entirely become part of the precipitate, some of the injected solvent volume is eventually lost to absorption into the surrounding tissue. Thus, Wallace does not teach a device which has a stable volume once implanted.

U.S. Pat. No. 5,712,252 (Smith) describes a method of augmenting soft tissue in a mammal which includes injecting keratin into soft tissue. Keratin is a biodegradable substance. U.S. Pat. No. 5,763,399 (Lee) describes a composition and method for effective revitalization of scar tissue by injecting a bioactive substance having angiogenic activity. The revitalization of scar tissue is intended to augment existing tissue. However, this invention cannot control the extent of augmentation.

U.S. Pat. No. 5,922,025 (Hubbard) describes a permanent, biocompatible material for soft tissue augmentation. The biocompatible material comprises a matrix of smooth, round, finely divided, substantially spherical particles of a biocompatible ceramic material. However, prevention of migration of the ceramic material is not described. U.S. Pat. No. 5,976,526 (Atala) describes treatment of vesicoureteral reflux, incontinence and other defects using an injectable preparation of bladder cells mixed with a liquid polymeric material. This material is susceptible to biodegradation. U.S. Pat. No. 5,855,615 (Bley at al) describes a composition for injecting into the urethra comprising a plurality of physiologically acceptable solid polymer particles dispersed in a physiologically acceptable bio-dissipatable liquid carrier. The solid polymer particles are capable of hydrating to a predetermined volume. The injection volume is therefore not necessarily the same as the final hydrated volume. U.S. Pat. No. 5,709,854 (Griffith-Cima et al) describes a cell polymeric solution that self-crosslinks for the purpose of inducing tissue formation.

One of the uses of the present invention is treatment of urinary incontinence. In particular, many women suffer from incontinence caused by childbirth or obesity. The initial treatment for stress incontinence is exercise to strengthen the pelvic floor muscles. If these exercises are ineffective, open surgical repair of the bladder neck is often attempted. Such surgical repair procedures are not successful for all patients. There is also risk associated with open surgical procedures, such as trauma, infection, and risks of anesthesia.

As an alternative to surgical repair, urinary incontinence has been treated by injecting various substances into the tissue surrounding the urethra, i.e., the periurethral tissue, to add bulk to this tissue. The aim of this treatment is to compress the urethra at the level of the bladder neck to impede involuntary flow of urine from the bladder. Murless has reported the use of sodium morrhuate for the treatment of stress incontinence (Murless, "The Injection Treatment of Stress Incontinence," J. Obstet. Gynaecol., 45:67-73 (1938).) This material was not successful in treating incontinence and pulmonary infarction was an observed complication. Paraffin and other sclerosing solutions have been tried, yielding poor results (Quackels, "Deux Incontinences Apres Adenomecomie Gueries Par Injection de Paraffine Dans Le Perince," "Acta Urol. Belg., 23:259-262 (1955); Sachse, "Treatment of Urinary Incontinence with Sclerosing Solutions: Indications, Results, Complications," Urol. Int., 15:225-244 (1963)).

Polytetrafluoroethylene (PTFE) particles (TEFLON™, POLYTEF™) have been used as injectable bulking material with a success rate from 30% to 86% in some studies (e.g., Politano, et al., "Periurethral Teflon Injection for Urinary Incontinence," J. Urol., 111:180-183 (1974); Lim, et al., "Periurethral Teflon Injection: A Simple Treatment for Urinary Incontinence," Br. J. Urol, 55:208-210 (1983); Schulman, et al., "Endoscopic Injection of Teflon to Treat Urinary Incontinence in Women," BMJ, 228:192 (1984); Rodriguez, "Late Results of the Endouretbral Injection of Teflon in Stress Urinary Incontinence," J. Urol. (Paris), 62:39-41 (1987); Vesey, et al., "Teflon Injection in Female Stress Incontinence. Effect on Urethral Pressure Profile and Flow Rate," Br. J. Urol., 62:39-41 (1988); Smart, "Poltef Paste for Urinary Incontinence," Aust. N. Z. J. Surg., 61:663-666 (1991).) The complications associated with PTFE injection have included foreign body granulomas which tended to migrate to distant organs, such as the lungs, liver, spleen and brain (Malizia, et al., "Migration and Granulomatous Reaction After Periurethral Injection of Polytef (Teflon)," JAMA, 251:3227-3281 (1984)).

Another injectable that has been used is glutaraldehyde cross-linked bovine dermal collagen (Stricker, et al., "Injectable Collagen for Type 3 Female Stress Incontinence: The first 50 Australian Patients," Med. J. Aust., 158:89-91 (1993); Capozza, et al., "Endoscopic Treatment of Vesico-Ureteric Reflux and Urinary Incontinence: Technical Problems in the Pediatric Patient," Br. J. Urol., 75:538-542 (1995).) A major problem with the use of collagen was biodegradation with associated decrease in implant volume over time necessitating retreatment. Collagen can also cause adverse immune responses and allergic reactions to bovine collagen have been described (Moore, et al., "Periurethral implantation of Glutaraldehyde CrossLinked Collagen (Contigen®) in Women with Type I or III Stress Incontinence: Quantitative Outcome Measures," Br. J. Urol., 75:359-363 (1995)).

Other materials have been suggested for use in the treatment of vesicourectal reflux. These substances include polyvinyl alcohol foam (Meriguerian, et al., "Submucosal Injection of Polyvinyl Alcohol Foam in Rabbit Bladder," J. Urol., 144:531-533 (1990)), glass particles (Walker, et al., "Injectable Bioglass as a Potential Substitute for Injectable Polytetrafluoroethylene," J. Urol, 148:645 (1992)), a chondrocyte-alginate suspension (Atala, et al., "Injectable Alginate Seeded with Chondrocytes as a Potential Treatment for Vesicoureteral Reflux," J. Urol., 150:745-747 (1993)) and a detachable silicone balloon (Atala, et al., "Endoscopic Treatment of Vesicoureteral Reflux with a Self-Detachable Balloon System," J. Urol., 148:724-728 (1992)).

Small poly-like nodules in the gastroesophageal tract can be removed by a procedure known as endoscopic mucosal resection (EMR). The nodule is first injected at its base with a solution that will decrease bleeding after the nodule is removed. The resulting bleb under the nodule raises the tissue and separates tissue layers, and thereby enables the doctor to remove it without damaging the rest of the esophagus or bowel. The EMR is done using a small cap that has a small wire loop which fits on the end of the endoscope. The nodule is suctioned into the cap and the wire loop is closed while cautery is applied. This is done so that the tissue can be examined under a microscope to determine if all of the cancer (or dysplasia) has been removed. If the cancer is not completely removed, additional visits may be needed to completely remove the cancer. When the nodule is completely removed, additional treatment can be done, such as photodynamic therapy if the nodule was cancerous.

Currently, this resection of the mucosal layer is done using a solution of saline to lift the mucosal layer so the polyp or nodule can be removed. One difficulty in the use of the saline is that it dissipates rapidly. The procedure can be much improved if a more viscous injectable were used. Preferably, the injectable would not migrate, and more preferably, it would act as a gel or solid once placed, to cap and protect the site after nodule removal.

Another example of space filling is treatment of the spinal disk. The spinal intervertebral disk comprises a fibrous support structure, the annulus fibrosis ("annulus"), a resilient structure connecting adjacent vertebrae, and the nucleus pulposus ("nucleus"), a gelatinous substance normally enclosed in a space formed by the annulus and the end plates of the vertebrae. Herniation of the disk involves partial failure of the annulus, and may allow part of the nucleus to protrude from the center of the disk. A contained disk herniation is one that is not associated with free nucleus fragments migrating to the spinal canal. However, even a contained disk herniation can still protrude and irritate surrounding structures, for example by applying pressure to spinal nerves. Escaped nucleus can chemically irritate neural structures.

Current treatment methods include reduction of pressure on the annulus by removing some of the interior nucleus pulposus material by percutaneous nucleotomy. See, for example, Kambin U.S. Pat. No. 4,573,448. Complications of nucleotomy include disk space infection, nerve root injury, hematoma formation, instability of the adjacent vertebrae and collapse of the disk from decrease in height. It has been proposed to treat weakening due to nucleus pulposus deficiency by inserting preformed hydrogel implants. See, Ray U.S. Pat. Nos. 4,772,287; 4,904,260 and, 5,562,736 and Bao U.S. Pat. No. 5,192,326.

Circumferential bulging of the spinal disk also can result in chronic disk weakening. The joint can become mechanically less stable. As the bulging disk extends beyond its normal circumference, the disk height is compromised and nerve roots are compressed. In some cases osteophytes form on the outer surface of the disk and further encroach on the spinal canal and channels through which nerves pass. This condition is known as lumbar spondylosis. Continued disk degeneration can result in one vertebral body segment approaching and possibly contacting an adjacent vertebral body segment.

Delivery of tissue adhesives to the spine in a minimally invasive manner has been disclosed, and includes procedures for restoring structural integrity to vertebral bodies. See Scribner U.S. Pat. Nos. 6,241,734 and 6,280,456; Reiley U.S. Pat. Nos. 6,248,110 and 6,235,043; Boucher U.S. Pat. Nos. 6,607,554 and Bhatnagar et al 6,395,007. Methods of repairing the spinal disk or portions thereof are disclosed in Cauthern U.S. Pat. No. 6,592,625, Haldimann U.S. Pat. No. 6,428,576, Trieu U.S. Pat. No. 6,620,196 and Milner et al U.S. Pat. No. 6,187,048.

Delivery of a liquid or low modulus prosthetic to the nuclear space requires constructing a passageway into the nucleus and removal of the nucleus, in total or in part. The passageway is usually made through the annulus, especially when part of the annulus must be removed to correct a pathological condition. Whether the passageway is through the annulus or elsewhere, for example, through the vertebral body, there is a risk of the nucleus prosthetic extruding through the passageway. Nucleus prosthetic extrusion can affect the surrounding nerves adversely. Methods of blocking a passageway made through the annulus are disclosed in Lambrecht U.S. Pat. No. 6,425,919, Lambrecht, et al. U.S. Pat. Nos. 6,482,235, 6,508,839, 6,821,276 and 6,883,520, and Cauthen U.S. Pat. No. 6,592,625. Other methods of preventing nucleus prosthetic extrusion include enclosing the prosthetic entirely inside of an enveloping sheath and are disclosed in Ray, et al. U.S. Pat. No. 4,904,260, Bao, et al. U.S. Pat. No. 5,192,326, Kuslich U.S. Pat. No. 5,549,679, Stalcup, et al. U.S. Pat. No. 6,332,894, Wardlaw U.S. Pat. No. 6,402,784, Weber, et al. U.S. Pat. No. 6,533,818, and Reuter, et al. U.S. Pat. No. 6,805,715. Still other methods of preventing nuclear prosthetic extrusion include delivering a preformed prosthetic in a reduced state, which when introduced into the body increases in volume. These methods and devices are disclosed in Ray et al. U.S. Pat. No. 6,602,291, Stoy et al. U.S. Pat. No. 6,726,721, and Li et al. U.S. Pat. No. 6,764,514.

Many other opportunities are available for the use of a space-filling material in medicine and surgery. Spaces that could be filled include the spaces left by lumpectomies and similar procedures, especially in the breast. Bulking can correct cosmetic defects, especially those due to aging; and bulking may have more demanding applications, such as bulking heart valves. Other uses in the body include vocal chord augmentation, filling wrinkles, treatment of gastroesophageal reflux, and replacement of the aqueous portion of the eye.

However, all of these applications require implantable materials, and as seen in the review above, there are problems with many of the materials being tested for these purposes, and there are few solutions actually in use in medical practice. Hence, there is an ongoing need for improved materials for these and other uses.

SUMMARY OF THE INVENTION

We have invented a method of making a novel improved polyurethane-based material which has a cluster of properties that are useful for soft tissue implants and other medical applications. The polyurethane backbone is a polyether polyol, also called a polyalkylene oxide (PAO), and consists essentially of a copolymer of ethylene oxide (EO) and propylene oxide (PO), preferably as a block copolymer of EO and PO (also known as a poloxamer). The polyalkylene oxide has an average functionality (i.e., number of isocyanate-reactive groups per polymer) greater than two, to enable branching or crosslinking, and preferably is predominantly or exclusively trifunctional. The polyalkylene oxide is endcapped with a difunctional isocyanate to form a polyisocyanate-capped urethane prepolymer, which is then reacted with water to form a shear-reversible gelling material. In the preferred methods of the invention, the urethane prepolymer is mixed with an excess of water to form a branched or partially crosslinked polymer of polyurethane urea. The method of mixing is a important step in the manufacture of the final reversibly-gelling polyurethane urea polymer ("RGP polymer").

To make the RGP polymer of the invention, in one embodiment the selected polyisocyanate-activated PAO ("prepolymer") is slowly added, for example by injection below the surface, to a vigorously sheared aqueous solution optionally comprising one or more of a non-reactive salt or buffer, a water-miscible organic solvent, and a non-reactive polymer, surfactant or other excipient material. The aqueous solution is stirred, pumped or otherwise agitated so as to provide a reproducible shear in the preparation. The prepolymer solution is injected into the aqueous solution at a rate slow enough to prevent the formation of macroscopic gel particles. The upper limit of the speed of addition is that speed at which macroscopically visible gel particles form in the solution. Below this limit, there is no visible gel formation at early stages of the process, although the viscosity of the solution increases.

As the concentration nears a percentage of about 5% to 8% in preferred embodiments, the polymer displays a novel effect, which is gelation on standing. After a sufficient amount of prepolymer solution has been injected, the solution continues to be stirred while the prepolymer is allowed to finish reacting, thereby producing a viscous, non-gelled polyurethane solution. The solution can be maintained for long periods as a liquid while stirring is continued. However, if prepolymer is added too rapidly, or if a limiting concentration is exceeded, the entire solution will form a non-reversible gel even while under shear.

After adding sufficient prepolymer and allowing it to react, then, when stirring or other agitation is stopped, the polyurethane solution gels. The gel, at 5%-8% concentration of polymer in the solution, is relatively weak, and is shear-sensitive. The gelation is sufficiently reversible under shear to allow the gelled solution to be forced through a syringe or similar device to reliquefy it, and to form a weak gel, at least at about body temperature, after dispensing. For example, the gelled solution can be drawn into a syringe, and promptly injected into a site at which formation of a gel is desired. The reversibly-gelling polyurethane polymer ("RGP polymer") of the invention can be used for any of a variety of medical procedures.

In a variant of this method, the viscosity of the prepolymer can be reduced by diluting the prepolymer with a non-isocyanate-reactive water-soluble or water-miscible material, such as an organic solvent, and then the diluted prepolymer is added to a stirred aqueous solution. The dilution reduces the incidence of gelation at the point of injection of the polymer into the aqueous solution.

In a second method, a polyisocyanate activated PAO ("prepolymer") is dissolved in a compatible, water-absorbing, non-reacting, non-aqueous, dry solvent, for example acetone. Then water or an aqueous solution as above is very slowly added to the solution, causing polymerization of the prepolymers to form a RGP polymer. After sufficient water has been added to achieve complete reaction of the active groups of the prepolymers, additional water or aqueous solution is added to swell the polymerized prepolymers and achieve at least a small excess of water in proportion to the amount of polyurethane. In particular, the water content is increased, initially or in stages, to give the final desired concentration of water in the RGP polymer preparation. The solvent is usually removed by evaporation, and the resulting aqueous solution of polyurethane will gel on standing and re-liquefy under shear.

The RGP polymer material can be concentrated by precipitation at an elevated temperature, for example about 50 to 55 deg. C. The precipitate can be collected, and optionally washed with 55 deg. C. water or other solution, and collected. The precipitate of RGP polymer will form a stiff gel on standing and will substantially or completely reliquefy under shear.

Thus, in one aspect the invention comprises a novel method of preparing a reversibly-gelling polyurethane polymer material, suitable for injection into a patient, the method comprising providing a polyisocyanate prepolymer, the prepolymer having a polyalkylene diol backbone comprising one or more copolymers having on average about 5 to about 30 mole % propylene oxide monomers and about 70 to about 95 mole % ethylene oxide monomers, and having an average functionality of greater than 2 active isocyanate groups per polymer molecule.

The reversibly-gelling polyurethane polymer may also be characterized as being miscible with water when sheared, and in being reversibly precipitable by elevated temperature, for example at a temperature above about 45 deg. C, and less than 100 deg. C. The gel In another aspect, the invention comprises a solution of a reversibly gelling polyurethane (RGP) polymer, made by dispersion of an isocyanate tipped polyalkylene oxide prepolymer ("prepolymer") into an aqueous solution at a rate sufficiently slow to prevent macroscopic gel formation, and in an amount sufficiently small that the solution does not gel while being stirred. The polyurethane gels on standing, but is easily sheared into a fluid, and re-gels on standing. The polyurethane can be used to treat medical or cosmetic conditions.

In another aspect, the invention is a material for treating medical and cosmetic conditions, and a method for using it. The material is a mixture containing about 1% to about 30% of a reversibly gelling polyurethane polymer, and about 99% to about 70% of water or an aqueous solution, characterized that at room and body temperatures the mixture gels on standing, but becomes fluid under shear. Generally, the conditions treated require the addition of bulk to a tissue site, or the filling of a void in tissue, or the reversible blockade of a passage in the body. Addition of bulk can be used in the treatment of incontinence, GERD and other sphincter disorders, and in the filling of tissues or tissue defects for functional purposes, such as for example a spinal disk. Injection between layers can be used to assist in the removal of polyps and other growths. Filling of voids and wrinkles, and selective bulking of tissue, is useful in cosmetic applications, including reconstructive measures after surgery or necrosis at a site. Temporary filling of passages can be useful in many situations, such as filling of the ear canal after treatment of the inner ear. The reversibly gelling polyurethane polymer can be used for separating tissue layers to facilitate removal of a growth from one of the layers, as in removal of polyps from the intestine, or of cancerous or disfiguring growths from the skin, or in similar situations in other parts of the body.

In particular, the invention is a method of making a shear-reversible polyurethane gel suitable for use in treatment of a medical or cosmetic condition, the method comprising the steps of providing a polyisocyanate prepolymer, the prepolymer having a polyalkylene oxide backbone comprising one or more copolymers having on average about 65 to about 95 mole % ethylene oxide monomers and at least about 5 to about 35 mole % propylene oxide monomers, and less than about 5% of any other monomer, having an average functionality of greater than 2 active isocyanate groups per prepolymer molecule; providing a reaction-supporting solvent, selected from a solution consisting essentially of water, a solution consisting essentially of a dry non-aqueous water-miscible organic solvent in which the prepolymer will dissolve, and a mixture thereof; shearing said reaction-supporting solvent so as to provide a known rate of shear; and when said reaction-supporting solvent contains water, infusing said prepolymer, optionally diluted with a dry non-reactive organic solvent, into said water solution at a rate slow enough to prevent the formation of macroscopic gel particles; or dissolving said prepolymer in said dry non-aqueous water-miscible organic solvent, and infusing one of water, and a mixture of water and solvent, into said solution of prepolymer in a dry non-aqueous water-miscible organic solvent, at a rate slow enough to prevent the formation of macroscopic gel particles; and finally allowing said prepolymer solution to finish reacting, thereby producing a reversibly gelling polyurethane (RGP) polymer solution. The RGP polymer gels when it is not sheared, and becomes fluid under shear.

The RGP can be concentrated to a concentration greater than about 8% by weight by precipitation of the polymer at a temperature in excess of about 45 deg. C. It is preferentially comprised of about 70% to about 75% by number of ethylene oxide monomers, and has a molecular weights in excess of about 4000 D. In synthesis, there is a limit of about 8% in maximal concentration of polymer during synthesis. Post-synthesis, the polymer can be concentrated to up to about 30%-35% by precipitation at a temperature above about 45 deg. C., and be used for any of the same uses.

The RGP polymer is used to treat a medical or a cosmetic condition. Treatment can involve bulking, space-filling, blocking, lubricating and coating of tissue, and implantation of a material into the body. Tissue bulking can be used for incontinence, gastroesophageal reflux (GERD), vesicoureteral reflux, tightening of the vagina, filling of vaginolabial folds, and non-closing heart valves, among other known uses. Space-filling uses include among others replacement of spinal nucleus material, temporary or semi-permanent filling of an internal cavity left after removal of a tumor or growth, and replacement of a vitreous or aqueous humor. Other uses include coating or lubrication of a tissue with an abraded surface, especially the skin, the dermis or a subdermal layer, or a surface of an organ after injury or surgery. Use can be in treatment of a cosmetic condition, for example filling of wrinkles, restoration of contours of facial features, filling of voids beneath the skin surface, and enhancement of the lips, breasts or other organs. An important use is for the implantation of a therapeutic material into the body. Particular operations include polyp removal, spinal disk repair, and bulking.

BRIEF DESCRIPTION OF THE FIGURE

FIG. 1 shows the viscosity of a gelled RGP polymer of the invention under shear in a viscometer at zero time, after 45 minutes of standing after shearing, and after standing for 18 hours.

DETAILED DESCRIPTION OF THE INVENTION

Polyurethanes are organic polymers made by reacting a polymeric polyol (in this application) or other reagents containing active hydrogen, such as amines, with an isocyanate. When the polyols are hydrophobic materials, the resulting material can be a tacky adhesive. If the polyols are selected properly, a polyurethane resin is formed, used to make certain types of plastic. The reaction of an isocyanate with a hydroxyl material liberates a carbon dioxide molecule, and this can be used to create bubbles in a reaction. Making polyurethane foam is accomplished by high shear mixing of a polyol and a polyisocyanate with water, resulting in a polyol cross-linked by isocyanate surrounding bubbles. All of these familiar commercial types of polyurethanes are made with hydrophobic, water-insoluble backbones, to avoid swelling of the plastic when in contact with water.

We have previously applied hydrophilic polyols activated with diisocyanates to tissue for various medical purposes (e.g., U.S. Pat. No. 6,254,327, U.S. Pat. No. 6,296,607; see full list supra). The reaction of the diisocyanate-tipped water-soluble polyols with water or saline, or with tissue, forms a polyurethane-based gel in-situ, which may be bonded to the tissue. Some of these applications, such as tissue bulking, could potentially be done using preformed polyurethanes, since strong adherence to the surrounding tissue is not necessary.

In the process of making improved tissue treating polyurethanes, we have discovered that by gradually adding certain kinds of polyisocyanate-capped polyols ("prepolymers") to water (or to an aqueous solution; herein "water" will include an aqueous solution, unless otherwise stated), or by very slowly adding water to a non-aqueous solution comprising polyol isocyanate prepolymers, we can form materials with unusual properties that are useful in tissue bulking, filling of voids, and similar uses.

Backbone Materials

For the polyol backbone, we use polyether polyols, also called polyalkylene oxides (PAO). (In this application, ethylene oxide as a backbone monomer is the same as ethylene glycol, and likewise propylene oxide and propylene glycol are equivalent) While ethylene oxide (EO), or ethylene glycol, can in principle be used as the sole alkylene oxide monomer in the polyol, the all-EO homopolymer (PEO, PEG) is prone to swell excessively, and is not suitable for the purposes of the invention. On the other hand, PAOs with about 40% or more (by number, i.e. mole fraction) of monomers derived from propylene oxide (PO) or butylene oxide (BO) or higher oxiranes, or trimethylene glycol, are too hydrophobic to swell sufficiently in water to form a gel that is suitable for in situ bulking. The range of about 5% to about 35% of non-EO monomers is broadly suitable for use in the invention, although with BO or other monomers more hydrophobic than PO, the upper limit is less. Preferred backbone polymers have about 5% to about 35% PO, preferably about 10% to about 30% PO, and essentially all of the rest EO, with perhaps a few percent of more hydrophobic monomers, alkylene oxide or other, being acceptable. Because the backbone polymer is endcapped by reaction with a di-isocyanate, which is hydrophobic, the maximum useable percentage of non-EO monomers will slowly increase as the inter-crosslink molecular weight increases, but is unlikely to be above about 35%. If spontaneously-degradable linkers are included, for example hydroxy carboxylic acids or amino acids, by capping the polyol with them before capping with isocyanate, then the maximum amount of non-EO subunits should be reduced, so that EO monomer content is at least about 70% and preferably 75% by number. On the other hand, the hydrophobic subunits provide much of the structure of a PAO-based polyurethane, and so a reasonable proportion of non-EO subunits is preferred. There is also a practical limitation, in that only a few ratios of EO:PO are available in commercial polymers.

The other variables are molecular weight, and degree and type of branching. We have obtained comparable results, in terms of physical properties, for polyols ranging from less than 4500 daltons to over 12,000 daltons (D). We have also used materials based on smaller segments (ca. 1000-1500 D) built up to be in the 4500-6000 D range. The latter are somewhat inferior, probably because they are conjugated with diisocyanate linking groups and so are somewhat more hydrophobic. It appears that an appropriate size for a backbone polymeric segment is a molecular weight of about 500 D or more, preferably more than 1000 D, more preferably about 4000 to about 16,000 D, and optionally up to at least 20,000 D and perhaps 50,000 D. (In this application, number-average MW, or alternatively the MW number on the label or fact sheet of a commercial product, is the default type of molecular weight value used.)

The average number of reactive groups per prepolymer molecule, for linking to other prepolymers, must be greater than 2 if the polyurethane is to be branched or crosslinked. In the current invention, the reaction product of the prepolymers is probably branched, and may be lightly crosslinked, and the number of reactive groups is greater than 2, preferably close to 3. We have used preparations in which polyalkylene diols have been at least partially "triolized" by endcapping with diisocyanate, followed by reaction with a small triol, such as trimethylol propane. However, it is simpler and more reproducible to use a standard trifunctional commercial material. Most of the work reported herein has been done with "Pluracol® 123" from Bayer, a tri-armed PAO with a hydroxyl number of 22.0-26.0 mg KOH/gm and primary hydroxyl (EO) ends. The nominal molecular weight, corresponding to the hydroxyl number and the triol structure, is 7000. The polyol is 75% EO: 25% PO. An alternative polyol is Bayer "Multranol® 9199", a triol with hydroxyl number about 36.5, estimated molecular weight about 4500 D; it also is 75% EO: 25% PO.

Isocyanates

Toluene diisocyanate, TDI, was obtained from BASF as Luparnate T80-1 (80:20 2,4- and 2,6-toluenediisocyanate). Isophorone diisocyanate (3-isocyanatomethyl-3,5,5,-trimethyl cyclohexyl isocyanate), IPDI, was obtained as Desmodur 1® from Bayer. These are the particular sources diisocyanates that have been used in the work described here. It is believed that most or all commercial preparation of TDI would be of essentially equal utility in the invention. It is probably that other known isocyanates can be used in the invention Our experiments with isophorone diisocyanate show somewhat less preferred properties, such as slower required addition rate, lower maximum content in water, or the like. Many isocyanates, not all of which are commercially available, are listed in our application US 2005-0215748, which is hereby incorporated by reference in its entirety. Since the exact results are believed to depend to some extent on the number of hydrophobic groups on the isocyanate, routine experimentation would be required to substitute other isocyanates into the examples described below.

Preparation of the Prepolymer

The method of preparation of reactive prepolymers from such materials is discussed in detail in our published application US 2005-0215748, incorporated by reference. Briefly, liquid PAOs are dried, and then mixed with slight excesses of small diisocyanates such as TDI and IPDI, and gently heated under nitrogen with stirring. Generally, no catalysts are used, and the reaction product can be used directly for treatment of tissue. The "prepolymer" reaction product is generally a viscous fluid, with a low level of color (clear to light yellow). The isocyanate-tipped PAOs can be stored for long periods if they are kept dry and shielded from light and air.

EXAMPLE 1

Preparation of a Prepolymer

A prepolymer was made by TDI endcapping of a block PAO triol. Multranol 9919. Triol (700.03 gm) was charged to a reactor and blanketed with argon. An overhead mixer was started and the reactor was closed, and an argon blanket was applied (1 SCFH continuously). The triol was dried at 120 deg. C. for about 24 hours, with stirring. Temperature was allowed to fall to room temperature (ca. 20-25 deg. C.), and then 88.68 g of toluene diisocyanate (TDI; Luparnate T-80.1) was added. The temperature was raised to 39.7 deg. C. over an hour. The reaction was continued for 24 days at 40 deg. C. with a blanket of 1 SCFH (ca. 0.5 liter/min at STP) of argon for 30 min. once a day. The final NCO (isocyanate) content was determined by standard methods (reaction with t-butyl amine and titration of unreacted t-butyl amine) as 2.71% by weight of the preparation. Viscosity was determined to be 8.050 cPs at 32.5 deg. C. Gel permeation chromatography produced an estimate of 55% triol, 26% dimerized triol, and 19% trimerized triol. The product was stored in dry bulk storage containers (glass jars with lids). Other examples of polymer preparation can be found in our issued and published patents cited above.

EXAMPLE 2

Methods of Preparation of the Reversibly Gelling Polyurethane Polymers of the Invention To form a RGP polymer of the invention, prepolymer 1, a liquid fast-reacting TDI-terminated triol made from Multranol® 9199 and described above, was slowly added to water (500 ml) which was being vigorously stirred in a glass reactor. Stirring was provided by a mechanical overhead high-torque mixer having two high shear mixing blades. The laboratory temperature was about 20 deg. C. The reaction should be performed below about 25 deg. C to prevent gel formation. Below 20 deg. C, the rate of addition of prepolymer to water should be adjusted downward in proportion to the temperature, for example, reduced to one half of the rate at 10 deg. C.

The prepolymer is added through a fine needle—typically 18 gauge—which may be driven by any suitable means, including without limitation a pump, pressure on a reservoir, or gravity. The precision of rate control of a syringe pump is preferred for experiments on this scale. The prepolymer was diluted with a non-reactive water-soluble solvent, in this experiment with an equal volume of acetone, to aid in the injection and dispersion of the prepolymer. The rate of addition of the prepolymer/acetone mixture to the water was 0.5 ml per hour in this experiment. Higher rates of addition, of this prepolymer without dilution, have been found to result in formation of conventional macroscopic gel beads. It is believed that this slow rate of addition is required for this reactive group because a thicker stream of added polymer will not dissipate in the water rapidly enough before polymerization. The limit may be dependent on the method of addition of the prepolymer to the water, and the key requirement appears to be that there be sufficient shear that the added material is completely dispersed in the water before it has time to crosslink significantly. (Hence, it is possible that the rate of addition could be increased with more vigorous dispersion of the prepolymer as it enters the aqueous phase.) There may also be a limitation on the total concentration of reactive groups in the solution, such that creation of a higher local concentration allows sufficiently rapid polymerization to form gels. (It should be recalled that in the polymerization of a polyisocyanate by water, an isocyanate that has reacted with a water molecule next reacts with an unreacted isocyanate group, forming a urea linkage; hence, the reaction rate increases with the square of concentration, other things being equal.)

The addition of prepolymer to the solution was continued until the total amount of prepolymer added to the water was 8.0%, or 40 ml prepolymer (plus 40 ml of acetone) for 500 ml of water. The addition of prepolymer was then terminated. If the polymer was diluted with acetone, as in the present experiment, the liquid preparation was stirred for 24 hours under flowing argon (as above) to allow acetone evaporation. If acetone was not used, no additional stirring would have been used. The finished polyurethane material was poured into jars and capped. The finished material gelled in the jars (or in the reactor if not promptly dispensed.)

There is an upper limit of monomer addition, above which the entire preparation forms a solid conventional gel. The upper limit for the above TDI triol is obtained when the volume of triol added reaches about 8% of the starting volume of the water—e.g., 8 ml added to 100 ml of water, or 80 for 1000. (Once the exact value is determined for particular lots of materials, it generally does not require change.) When the amount added nears the upper limit, opalescence appears in the solution where the polymer is being added, perhaps due to trapping of bubbles of evolved carbon dioxide. The exact limit can be determined by titration of smaller aliquots until they gel. Alternatively, it is not required that the actual limit to be reached in order to obtain the product of the invention, so the addition of prepolymer can be stopped at, for example, 90% or 95% of the limiting amount, or upon viewing of opalescence. Once addition is stopped, the solution should continue to be stirred until the reaction is complete. This is at most 5 minutes for TDI, but can be over half an hour for IPDI, and must be adjusted by experiment for other diisocyanates.

After stirring stops, the distinctive property of the novel RGP polymer becomes evident: the solution gels. However, the gel is very soft, and the preparation re-liquefies readily on stirring or mild shear. For example, the gel can be sucked up into a syringe without obviously fracturing. The solution in the syringe is initially liquid, as judged by the movement of air bubbles, but gradually re-gels.

EXAMPLE 3

Preparation of Gels from Prepolymer Diluted in Solvent

Prepolymer was diluted 1:1 with acetone (80 ml of prepolymer and 80 ml of acetone). A flask containing 1000 ml of isotonic saline, and a stir bar, was placed on a magnetic stirrer, and the saline was stirred vigorously. The prepolymer/acetone solution was injected at the rate of about 0.5 ml/hr until completion, over a period of about 15 days. The preparation was observed periodically for any formation of gel at the tip of the syringe needle, which was removed if found. After all of the prepolymer/acetone solution had been injected, and stirring had been continued for at least a day, the preparation was placed in a hood and stirred until the acetone had evaporated. Then the finished polymer was dispensed and allowed to gel. This preparation is somewhat more forgiving than that of example 2, in part because the dilution with non-reactive solvent reduces the viscosity of the polymer and allows it to disperse in the water more rapidly.

EXAMPLE 4

Re-Gelation after Shear

In FIG. 1, an experiment is shown in which the gel is allowed to gel in a viscometer, and then the viscosity is measured at successively higher shear rates (spindle RPM). The viscometer was a Brookfield DVII+Pro, with a #25 spindle, and a thermostatted water circulator bath for temperature control. The spindle and a disposable cup were placed dry into the "small sample" receiver/adaptor. The spindle was affixed, and the sample (ca. 18 ml) was then placed into the disposable cup. It was allowed to equilibrate at 32.5 deg. C. for at least about 4 hours, or overnight. To measure a viscosity vs. shear curve, the spindle was rotated for the longer of 6 revolutions or 2 minutes, and the temperature, viscosity, and torque (% of range) were recorded. Two more measurements were made at the same shear rate. Then the next higher speed was tested. The complete test took nearly 2 hours.

The material of Example 2 was tested three times while remaining in the sample cup. In the first run, a curve was obtained (diamonds) in which the viscosity was initially over 140,000 cP and gradually dropped with increasing shear and time. The spindle was turned off, and the system was allowed to re-gel for 45 minutes. The shearing curve was then re-measured (squares). The viscosity was significantly lower at each viscosity value above about 5000 cP. The spindle was again turned off, and the system was allowed to re-gel overnight (ca. 16 hrs.). The shear curve was again measured (triangles). The third curve matched the starting curve at most shear values, and was close even at the lowest shear rates. This result is taken to indicate that the gel formed is truly a non-covalent gel, because it is reversible on shear. The weaker gel seen at shorter times (squares) reflects the time needed to completely re-form the gel. It is believed that these effects demonstrate that most of the variable viscosity of the preparation is based on reversible bonding between polymers, rather than on covalent bonds between polymers.

It should be emphasized that the polymeric structures in the solutions or gels of the invention do not scatter light appreciably, unless they have been precipitated (see below). Some structure can be seen during pouring, by trapping of bubbles. There is no observable haze or significant angle-dependence of color of light for the material of Example 2. These effects are consistent with a material that is in the form of an interactive polymer, rather than a gel particle.

Without wishing to be bound by a theory, we conjecture that in this system the reactive groups on the prepolymer find each other in the water and react, and so the viscosity of the preparation gradually increases during the addition, both because of increased average PAO concentration and because of chain extension of the polymers, with perhaps very limited crosslinking between or within polymers. It seems likely that the polymers formed are predominantly linear or, because of the triol structure, branched. There may be localized crosslinking within chains. This could account for the existence of concentration limits—when the concentration of reactive groups is below a threshold, growing molecules tend to self react, while above that limit, inter-chain reactions rapidly leads to bulk crosslinking and gelation.

EXAMPLE 5

Synthesis of RGP Polymer in Organic Solvent

In a reactor at room temperature, 500 ml acetone (dry, reagent grade) was vigorously agitated with a magnetic stir bar at room temperature, about 20 degrees C. Then 40 ml of the polymer preparation of Example 1 is added to the acetone. After the prepolymer has completely dissolved into the acetone, 10 ml of water was added. Bubbles caused by $CO_2$ release were observed. After stirring for 24 hours with a lid on the mixture to prevent acetone evaporation (and optionally, blanketing with inert gas), an additional 10 ml of water was added. Stirring was continued for 24 hours, and again 10 ml of water was added. This step was repeated until $CO_2$ release was no longer observed. In this experiment, 10 days was required. On the $10^{th}$ day, 500 ml of water was added. The mixture was warmed to 30 degrees C. in a fume hood, and stirred until the acetone had evaporated. Water was added periodically to maintain the solution at about 500 ml. volume. The evaporation was continued until there was no longer any odor of acetone. The material gelled immediately when not stirred.

Aside from requiring more organic solvent, this preparation method is more forgiving than the previous two procedures. This may be because the locally high concentration of water, in the low-viscosity acetone solution, causes polymerization of the prepolymer in a low concentration environment, favoring branched and internally linked polymers of the prepolymers, rather than spatially extensive gels.

EXAMPLE 6

Production of High Concentration Polyurethane Reversible Gel

Because 8% is an approximate upper limit of concentration during preparation, at least by the current procedure, it can be efficient to make the polyurethane product at a lower concentration, such as 4% or 5%, when such a concentration is sufficient for the intended use. Exceeding the upper limit rapidly results in the conversion of the entire preparation into a macroscopic, irreversible gel.

If desired, a firmer shear-reversible gel can be obtained by concentrating a solution obtained as above, rather than by direct synthesis. If a solution of the sort described above, having for example 2% to 8% polyurethane polymer, and gelling at room temperature or 37 deg. C., is heated with vigorous stirring to about 55 deg. C., it precipitates from solution as white flakes. These can be harvested at elevated temperature, and will melt at room temperature. The material is conveniently harvested by pouring off the solvent, and can be dissolved in water and reheated for additional purification. The resulting solution contains about 2 grams of water for every gram of polymer, without any significant effect apparent of the initial concentration of polymer in the solution.

Procedure for Precipitate Polymer:
1. Produce a solution of between 2 and 8% polymer solution. The solution may comprise water and/or solvent (e.g., acetone).
2. Heat while stirring until phase separation (at approximately 55 deg. C.).
3. Pour off top layer (water and/or solvent).
4. Allow to cool; the precipitated polymer returns to a clear, shear-thinning gel state
5. If acetone is used, the acetone may be extracted by washing the gel in either saline or water until the acetone is extracted to the desired level. Washing consists of placing the gel in a bath of water at room temperature, e.g. 22 deg. C., and letting it equilibrate, for example for 1 hour, and then reprecipitating it by heating.
6. Pour off water layer, and repeat if required.

The material obtained by this method has a solids content in the range of 30-35%. It is believed that this concentration can be made more precise by careful temperature control and standardization of protocols. It is anticipated that the equilibrium concentration will prove to be a function of the detailed makeup of the RGP polymer.

Physical Properties of the Product

The RGP polymers of the invention are gels at or near body temperature (i.e., above about 35 deg. C.). At the typical concentrations of synthesis (about 5% to about 8%), the polymers are typically soft gels at room temperature, ca. 20-25 deg. C., or below. The gels can be frozen and thawed. As noted, the gels precipitate on heating.

The gels can carry compatible particulate solids. The solids may be biodegradable or absorbable. Such a property could be useful for suspending contrast agents, or particles for inducing bone growth, or other particulates useful in medicine. As an example, a volume of gel was mixed with 10% of the volume of 0.3 micron tantalum powder (contrast medium). The gel/tantalum mixture was sheared in a syringe to homogenize it, and then the mixture was allowed to stand. It was observed to re-gel on standing. The tantalum powder was seen to be uniformly distributed in the gel.

The gels are stable for at least 1 year when stored at room temperature (ca. 20-25 degrees C.), when protected from evaporation of water, and from strong or continuous light. At room temperature, protection from growth of bacteria and mold is required. The gels can be frozen and thawed without noticeable change of properties. In the frozen state, there may be an increase in the content of bubbles in the gel. On thawing, there is no phase separation, or loss of ability of the polymer to bind water, and the frozen samples seemed essentially unchanged.

Based on the above observations, there is only a minor effect of adding a water-soluble solvent to either the polymer or the water during the polymerization process. It therefore seems likely, as a working hypothesis, that the polymerized prepolymer differs from a conventional gel by being crosslinked in a "dilute" way. Thus, the growing polyurethane urea chains, which will grow slowly compared to growing chains in an environment high in water, may tend to form chains that are at least partially linear and branched, rather than being covalently crosslinked. This could create a polymer solution that forms weak macroscopic gels, and is able to gradually re-gel via re-entanglement of long, branched chains on standing. Such a gel could be sheared and then return to an equilibrium gelled structure over time.

Uses of the Invention

One distinguishing feature of the innovative polyurethane material is that it is an inert, non-reactive polymeric material that forms gels at body temperature, and usually at room temperature. The gelled form of the material can, in the physiological range (0-37 deg. C.), be sheared to form a liquid, or a flowable material containing less gel structure and the liquid or flowable gel, on standing in temperatures of about 10-37 deg. C., will re-form a gel with similar properties to the gel that was sheared. No chemical reactions occur during these conversions, so the material is very safe. Because the gelation is reversible, the RGP polymer is readily removable if required.

These materials are intended for, and believed to be suitable for, use as bulking, space-filling, blocking, lubricating or coating uses in treating medical and cosmetic conditions. As noted above, many opportunities are available for the use of a space-filling material in medicine and surgery. Spaces that could be filled include the spaces left by lumpectomies and similar procedures, especially in the breast; and bulking may have more demanding applications, such as bulking heart valves. Addition of bulk can be used in the treatment of incontinence, treatment of gastroesophageal reflux (GERD), vesicourectal reflux and other sphincter problems. Several uses are described in more detail in the Background section above.

Other uses in the body include vocal chord augmentation, and replacement of the aqueous portion of the eye. Injection between layers can be used to assist in the removal of polyps and other growths, both from internal organs such as the intestine, and in plastic surgery and dermatology. Injection in selected sites can provide a temporarily highly conductive or poorly conductive layer, where required in surgery or electrosurgery. Filling of voids is useful in cosmetic applications, including reconstructive measures after surgery or necrosis at a site, or filling of wrinkles and other skin defects, for example due to aging. Other voids can be filled for functional purposes, such as a spinal disk. Temporary filling of passages can be useful in many situations, such as filling of the ear canal after treatment of the inner ear. Lubrication can be enhanced by the gel, for example in joints. The material can be used as a dressing for wounds, burns or dermatological conditions, where it can be applied as a liquid at room to body temperature, and will gel after application without requiring any covalent chemical reaction.

Because the RGP polymer can be sheared at room or body temperature and then re-gel, a gel can be prepared that is isotonic and contains selected biologically important materials, including not only conventional nutrients, but proteins, nucleic acids, and cells. Because the gel is not covalently linked and is chemically inert, cells can proliferate in it and both receive and generate biological signals. Thus, regeneration of organs, long-term generation of important cellular products, and execution of other difficult biomedical procedures are possible using the gels of the invention as reversible supports.

In the spine, the RGP polymer can be concentrated to a selected concentration and then used as a nucleus replacement material after partial or complete nuclectomy. As described elsewhere, the prepolymer can be used to repair an annulotomy made to give access to the nucleus, or a defect in the annulus that allowed nuclear displacement.

The invention has been described in several embodiments to assist in its understanding, but equivalents within the scope of the invention will be apparent to those skilled in the relevant arts. The scope of the invention is not limited by the embodiments disclosed, but only by its claims.

The invention claimed is:

1. A method of making a shear-reversible polyurethane gel suitable for use in treatment of a medical or cosmetic condition, the method comprising the steps of:
    a) providing a polyisocyanate prepolymer, the prepolymer having a polyalkylene oxide backbone comprising one or more copolymers having on average about 65 to about 95 mole % ethylene oxide monomers and at least about 5 to about 35 mole % propylene oxide monomers, and less than about 5% of any other monomer, having an average functionality of greater than 2 active isocyanate groups per prepolymer molecule;
    b) providing a reaction-supporting solvent, selected from a solution consisting essentially of water, a solution consisting essentially of a dry non-aqueous water-miscible organic solvent in which the prepolymer will dissolve, and a mixture thereof;
    c) shearing said reaction-supporting solvent so as to provide a known rate of shear; and
    d) either
        i) when said reaction-supporting solvent contains water, infusing said prepolymer, optionally diluted with a dry non-reactive organic solvent, into said water solution at a rate slow enough to prevent the formation of macroscopic gel particles; or
        ii) dissolving said prepolymer in said dry non-aqueous water-miscible organic solvent, and infusing one of water, and a mixture of water and solvent, into said solution of prepolymer in a dry non-aqueous water-miscible organic solvent, at a rate slow enough to prevent the formation of macroscopic gel particles; and
    e) allowing said prepolymer solution to finish reacting, thereby producing a reversibly gelling polyurethane (RGP) polymer solution;
    characterized in that the polyurethane solution gels when it is not sheared, and becomes fluid under shear.

2. The method of claim 1 further comprising the step of concentrating the RGP polymer to a concentration greater than about 8% by weight by precipitation of the polymer at a temperature in excess of about 45 deg. C.

3. The method of claim 1 where the polyalkylene oxide polymers used to make the prepolymer comprise about 70% to about 75% by number of ethylene oxide monomers.

4. The method of claim 1 where the polyalkylene oxide-based prepolymers used to make the RGP polymer have molecular weights in excess of about 4000 D.

5. The method of claim 1 wherein the RGP polymer formed by reaction of the prepolymers comprises less than about 8% of the solution at the completion of the reaction.

6. The use of the product of any one of claims 1-5 to treat a medical or a cosmetic condition.

7. The use of claim 6, where the use is selected from bulking, space-filling, blocking, lubricating and coating of tissue, and implantation of a material into the body.

8. The use of claim 7 where the use is for bulking and the condition that is treated by tissue bulking is selected from incontinence, gastroesophageal reflux (GERD), vesicoureteral reflux, tightening of the vagina, filling of vaginolabial folds, and non-closing heart valves.

9. The use of claim 7 where the use is for space-filling and the condition that is treated is selected from replacement of spinal nucleus material, temporary or semi-permanent filling of an internal cavity left after removal of a tumor or growth, and replacement of a vitreous or aqueous humor.

10. The use of claim 7 wherein the use is for coating or lubrication of a tissue with an abraded surface, selected from the skin, and a surface of an organ after injury or surgery.

11. The use of claim 6 where the cosmetic condition is selected from filling of wrinkles, restoration of contours of facial features, filling of voids beneath the skin surface, and enhancement of the lips, breasts or other organs.

12. The use of claim 6 for the treatment of a condition affecting the dermis or a sub-dermal layer.

13. The use of claim 6 wherein the use is the implantation of a therapeutic material into the body.

14. A method for treating a growth of the bowel, the method comprising the steps of
    a) accessing the bowel having the growth, by open or colonoscopic techniques;

b) injecting a gel-forming material between the mucosa and the muscule layer to isolate the growth from the muscle layer; and c) placing a snare around the growth and removing the growth;

wherein the gel is a RGP polymer which forms a gel in a temperature range which includes body temperature, said gel being liquefiable in a reversible way by shear and further being capable of re-gelling after injection beneath the growth.

15. A method for treating a growth of the skin, the method comprising the steps of:

a) injecting a gel-forming material within the skin to isolate the growth from the lower layers of the skin; and b) removing the growth;

wherein the gel is a RGP polymer which forms a gel in a temperature range which includes body temperature, said gel being liquefiable in a reversible way by shear and further being capable of re-gelling after injection beneath the growth.

16. A method for treating a tissue defect by bulking the tissue, the method comprising the steps of a) accessing the defective site by open or minimally invasive techniques; and b) injecting gel into the area to be augmented at one or more sites until the desired geometry is obtained;

wherein the gel is a RGP polymer which forms a gel in a temperature range which includes body temperature, said gel being liquefiable in a reversible way by shear and being capable of re-gelling after administration into the area to be augmented.

17. A method for treating a defect in a spinal disk, the method comprising the steps of a) accessing the defective disk by open or minimally invasive techniques;

b) removing protruding or damaged portions of the disc; and c) injecting gel into cavities formed in the disc to restore the disc's function;

wherein the gel is a RGP polymer which forms a gel in a temperature range which includes body temperature, said gel being at least partially liquefiable in a reversible way by shear and being capable of re-gelling after administration into the area to be augmented.

18. A hydrogel formed from a reversibly gelling polyurethane (RGP) polymer, characterized in that:

the RGP polymer is a product of the reaction of at least one polyisocyanate-substituted polyetherpolyol prepolymer, having average functionality greater than two, with water, under conditions of high shear;

the hydrogel contains at least about 50% water at equilibrium; and the hydrogel can be mechanically sheared into a fluid material that re-forms a gel on standing.

19. The hydrogel of claim 18 where on average, at least about 65% of the monomers comprising the gelling polymers are ethylene oxide based monomers.

20. The hydrogel of claim 18 further characterized in having a phase transition to a precipitated gel phase having a decreased water content at a temperature in the range of about 45 deg. C. to about 100 deg C.

21. The hydrogel of claim 18 wherein the reaction is performed by adding the polyisocyanate-substituted polyetherpolyol polymer to a stirred water-based solution at a rate sufficiently slow to avoid macroscopic gelation.

22. The hydrogel of claim 21 wherein addition of the polyisocyanate-substituted polyetherpolyol polymer is limited to a maximum value of 8% of the starting weight of the solution.

23. The hydrogel of claim 18 wherein the reaction is performed by dissolving the polyisocyanate-substituted polyetherpolyol polymer in an anhydrous nonaqueous solvent, forming a solution, and then adding water to said solution while it is stirred, at a rate of addition sufficiently slow to avoid macroscopic gelation.

24. A concentrated reversibly gelling polyurethane polymer preparation based on a prepolymer of a polyisocyanate-substituted polyetherpolyol polymer, prepared by warming the preparation of claim 18 sufficiently to precipitate the reversibly gelling polyurethane polymers; collecting said material at a temperature elevated sufficiently for the material to remain precipitated; and allowing said precipitated polyurethane polymer to melt at a lower temperature, thereby obtaining a more concentrated solution.

25. The use of the product of claim 24 for the treatment of a medical or cosmetic condition.

26. The use of the product of claim 24 for forming a depot containing a therapeutically effective material.

27. The use of the product of claim 24 for the regeneration of tissues.

* * * * *